United States Patent [19]

Thomas et al.

[11] Patent Number: 5,245,035

[45] Date of Patent: Sep. 14, 1993

[54] HETEROCYCLIC BORON COMPOUNDS AS INTERMEDIATES FOR ANGIOTENSIN II ANTAGONISTS

[75] Inventors: Andrew P. Thomas, Congleton; David M. G. Martin, Stockport; Stanley A. Lee, Macclesfield; Lyn Powell, both of Macclesfield, all of England

[73] Assignee: Imperial Chemical Industries PLC, London, England

[21] Appl. No.: 822,479

[22] Filed: Jan. 17, 1992

[30] Foreign Application Priority Data

Jan. 17, 1991 [GB] United Kingdom ................ 9100995
Apr. 2, 1991 [GB] United Kingdom ................ 9106877
Oct. 14, 1991 [GB] United Kingdom ................ 9121733

[51] Int. Cl.$^5$ ........................................ C07D 215/233
[52] U.S. Cl. ..................................... 546/153; 546/290; 546/301; 546/303
[58] Field of Search ................ 546/154, 290, 301, 303

[56] References Cited

FOREIGN PATENT DOCUMENTS 253310 1/1988 European Pat. Off. .
0412848 2/1991 European Pat. Off. .
0453210 10/1991 European Pat. Off. .

OTHER PUBLICATIONS

H. R. Snyder et al. "Synthesis of Aromatic Boronic Acids, Aldehydo Boronic Acids and a Boronic Acid Analog of Tyrosine" *J. Amer. Chem. Soc.* (1958), 80, 835–838.

N. Miyaura et al. "The Palladium-Catalyzed Cross--Coupling Reaction of Phenylboronic Acid with Haloarenes in the Presence of Bases" *Synth. Commun.* (1981), 11, 513–519.

*Primary Examiner*—Howard T. Mars
*Assistant Examiner*—Michael B. Hydorn
*Attorney, Agent, or Firm*—Thomas E. Jackson

[57] ABSTRACT

The invention concerns novel boron compounds of the formula IV, in which Q, $Y^1$, $G^1$ and $G^2$ have the various meanings defined herein, and their acid and base addition salts. The said compounds are useful in the manufacture of certain quinoline, pyridine and imidazole derivatives which have angiotensin II inhibitory activity. The invention also provides novel processes for the production of the quinoline, pyridine and imidazole derivatives.

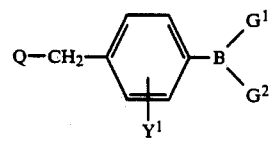

7 Claims, No Drawings

HETEROCYCLIC BORON COMPOUNDS AS INTERMEDIATES FOR ANGIOTENSIN II ANTAGONISTS

This invention concerns novel boron compounds and, more particularly, novel boron compounds which contain quinoline, pyridine or imidazole groups which compounds are useful as chemical intermediates in the production of certain quinoline, pyridine and imidazole derivatives, which derivatives possess pharmacologically useful properties in antagonising at least in part one or more of the actions of substances known as angiotensins, and in particular of that known as angiotensin II (hereinafter referred to as "AII"). The invention also concerns novel processes for the production of said quinoline, pyridine and imidazole derivatives.

The angiotensins are key mediators of the renin-angiotensinaldosterone system, which is involved in the control of homeostasis and fluid/electrolyte balance in many warm-blooded animals, including man. The angiotensin known as AII is produced by the action of angiotensin converting enzyme (ACE) from angiotensin I, itself produced by the action of the enzyme renin from the blood plasma protein angiotensinogen. AII is a potent spasmogen especially in the vasculature and is known to increase vascular resistance and blood pressure. In addition, the angiotensins are known to stimulate the release of aldosterone and hence result in vascular congestion and hypertension via sodium and fluid retention mechanisms. AII inhibitors are useful for the reduction or prevention of these effects produced by the action of AII. Although a number of AII inhibitors are known, there remains a continuing need for alternative inhibitors and for effective synthetic procedures for the production of both new and known AII inhibitors. The present invention provides a means for obtaining both new and known AII inhibitors.

In our co-pending European Patent Application, Publication No. 412848, there is described a series of quinoline derivatives (possessing AII antagonist properties) of formula I (set out hereinafter) wherein $R^1$ is hydrogen, (1–8C)alkyl, (3–8C)cycloalkyl, phenyl or substituted (1–4C)alkyl, the latter containing one or more fluoro substituents or bearing a (3–8C)cycloalkyl, hydroxy, (1–4C)alkoxy or phenyl substituent; $R^2$ is hydrogen, (1–8C)alkyl, (3–8C)cycloalkyl, (3–8C)cycloalkyl-(1–4C)alkyl, carboxy, (1–4C)alkoxycarbonyl, cyano, nitro, phenyl or phenyl(1–4C)alkyl; $R^3$ and $R^4$ are independently selected from hydrogen, (1–4C)alkyl, (1–4C)alkoxy, fluoro(1–4C)alkoxy, halogeno, hydroxy, trifluoromethyl, cyano, nitro, amino, (1–4C)alkanoylamino, alkylamino and dialkylamino of up to 6 carbon atoms, dialkylamino-alkyl of 3 to 8 carbon atoms, (1–4C)alkanoyl, carbamoyl, N-alkylcarbamoyl and di-(N-alkyl)carbamoyl of up to 7 carbon atoms, carboxy, (1–4C)alkoxycarbonyl, (1–6C)alkylthio, (1–6C)alkylsulphinyl, (1–6C)alkylsulphonyl, and substituted (1–4C)alkyl, the latter bearing an amino, hydroxy or (1–4C)alkoxy substituent; or $R^3$ and $R^4$ together form (1–4C)alkylenedioxy attached to adjacent carbon atoms of the benzene moiety of formula I; Ra and $R^5$ are independently selected from hydrogen, (1–4C)alkyl, (1–4C)alkoxy, halogeno, trifluoromethyl, cyano or nitro; A is methylene; X is phenylene optionally bearing a substituent selected from (1–4C)alkyl, (1–4C)alkoxy, halogeno, trifluoromethyl, cyano and nitro, or X is a direct bond between the adjacent phenyl group and moiety A; Za is 1H-tetrazol-5-yl, —CO.NH.(1H-tetrazol-5-yl) or a group of the formula —CO.OR$^6$ or —CO.NH.SO$_2$.R$^7$ in which $R^6$ is hydrogen or a non-toxic, biodegradable residue of a physiologically acceptable alcohol or phenol, and $R^7$ is (1–6C)alkyl, (3–8C)cycloalkyl or phenyl; and wherein any of said phenyl moieties may be unsubstituted or bear one or two substituents independently selected from (1–4C)alkyl, (1–4C)alkoxy, halogeno, cyano and trifluoromethyl; or a non-toxic salt thereof; but excluding methyl 2-[(3-methoxycarbonylquinolin-4-yloxy)methyl]benzoate.

A specific value for X which is of particular interest is, for example, p-phenylene.

A preferred value for $R^5$ is, for example, hydrogen and for $R^1$ is, for example, methyl, ethyl or propyl.

An especially preferred value for Za is, for example, 1H-tetrazol-5-yl and, in particular, when it is attached ortho to the group X.

Compounds disclosed in our said co-pending application which are particularly preferred are 2-methyl-4-[(2'-(1H-tetrazol-5-yl)biphenyl-4-yl)methoxy]quinoline, 2-ethyl-4-[(2'-(1H-tetrazol-5-yl)biphenyl-4-yl)methoxy]quinoline, 2-ethyl-7-hydroxymethyl-4-[(2'-(1H-tetrazol-5-yl)biphenyl-4-yl)methoxy]quinoline, 2-ethyl-6-(2-fluoroethoxy)-4-[(2'-(1H-tetrazol-5-yl)biphenyl-4-yl)methoxy]-quinoline, 2-ethyl-6-(2,2,2-trifluoroethoxy)-4-[(2'-(1H-tetrazol-5-yl)biphenyl-4-yl)methoxy]-quinoline and 2-ethyl-6-isopropoxy-4-[(2'-(1H-tetrazol-5-yl)biphenyl-4-yl)methoxy]quinoline, together with their non-toxic salts.

We are also aware, for example as described in our separate co-pending application, publication no. 453210, of a series of pyridine derivatives (possessing AII antagonist properties) of formula II (set out hereinafter) wherein $T^1$ is hydrogen, (1–8C)alkyl, (3–8C)cycloalkyl, phenyl or substituted (1–4C)alkyl, the latter containing one or more fluoro substituents or bearing a (3–8C)cycloalkyl, (1–4C)alkoxy or phenyl substituent; $T^2$ is hydrogen, (1–8C)alkyl, (3–8C)cycloalkyl, (3–8C)cycloalkyl-(1–4C)alkyl, carboxy, (1–4C)alkoxycarbonyl, (3–6C)alkenyloxycarbonyl, cyano, nitro, phenyl or phenyl(1–4C)alkyl; $T^3$ is selected from halogeno, (1–4C)alkoxy, amino, alkylamino and dialkylamino of up to 6 carbon atoms, and any of the values defined for $T^1$; $T^4$ is selected from hydrogen, (1–4C)alkyl optionally bearing an amino, (1–4C)alkanoylamino, phenylcarbonylamino, hydroxy or (1–4C)alkoxy substituent, carboxy, (1–4C)alkoxycarbonyl, (3–6C)alkenyloxycarbonyl, cyano, nitro, carbamoyl, (1–4C)alkanoyl, N-alkylcarbamoyl and di-(N-alkyl)carbamoyl of up to 7 carbon atoms, formyl, halogeno, amino, alkylamino and dialkylamino of up to 6 carbon atoms, 3-(1–4C)alkylureido and (1–4C)alkanoylamino; or $T^4$ is a group of the formula -A$^1$.A$^2$.E wherein A$^1$ is carbonyloxy, A$^2$ is (1–6C)alkylene and E is selected from hydroxy, (1–4C)alkoxy, phenyloxy, phenyl(1–4C)alkoxy, pyridyl(1–4C)alkoxy, 4-morpholino(1–4C)alkoxy, phenylamino, amino, alkylamino and dialkylamino of up to 6 carbon atoms, (1–4C)alkanoylamino, (1–4C)alkylsulphonylamino, phenylsulphonylamino, sulphamoylamino (—NH.SO$_2$.NH$_2$), carboxamidomethylamino (—NH.CH$_2$.CO.NH$_2$), (1–4C)alkanoyloxy, phenylcarbonyloxy, aminocarbonyloxy (—O.CO.NH$_2$), (1–4C)alkylaminocarbonyloxy, carboxy, (1–4C)alkoxycarbonyl, carbamoyl, N-alkylcarbamoyl and di-(N-alkyl)carbamoyl of up to 7 carbon atoms, (1–4C)alkanoyl, 4-morpholino, 1-imidazolyl and succinimido group; or E is a group of the formula -A$^3$.E$^1$ wherein $A^3$ is oxy, oxycarbonyl or imino and $E^1$ is a 5 or 6-membered saturated or unsaturated heterocyclic ring containing 1 or 2 nitrogen atoms and linked to $A^3$ by a ring carbon atom; or $A^3$ is oxycarbonyl and $E^1$ is a 4-morpholino group or a 5 or 6-membered saturated heterocyclic ring containing 1 or 2 nitrogen atoms, optionally bearing a (1–4C)alkyl group and linked to $A^3$ by a ring nitrogen atom; and wherein $E^1$ the remainder of the ring atoms are carbon; or $T^3$ and $T^4$ together form (3–6C)alkylene, one of the methylene groups of which may optionally be replaced by a carbonyl group, or (3–6C)alkenylene; $T^5$ is hydrogen; $T^6$ is hydrogen or (1–4C)alkyl; $T^7$ is selected from hydrogen, (1–4C)alkyl, (1–4C)alkoxy, halogeno, trifluoromethyl, cyano and nitro; U is phenylene optionally bearing a substituent selected from (1–4C)alkyl, (1–4C)alkoxy, halogeno, (1–4C)alkanoyl, trifluoromethyl, cyano and nitro, or U is a direct bond between the adjacent phenyl group and the carbon atom bearing $T^5$ and $T^6$; Zb is 1H-tetrazol-5-yl, —CO.NH.(1H-tetrazol-5-yl) or a group of the formula —CO.O$T^8$ or —CO.NH.SO$_2$.$T^9$ in which $T^8$ is hydrogen or a non-toxic, biodegradable residue of a physiologically acceptable alcohol or phenol, and $T^9$ is (1–6C)alkyl, (3–8C)cycloalkyl or phenyl; and wherein any of said phenyl moieties may be unsubstituted or bear one or two substituents independently selected from (1–4C)alkyl, (1–4C)alkoxy, halogeno, cyano and trifluoromethyl; or an N-oxide thereof; or a non-toxic salt thereof.

A specific value for U which is of particular interest is, for example, p-phenylene.

A preferred value for $T^1$ or $T^3$ is, for example, methyl or ethyl.

A preferred value for $T^2$ is, for example, hydrogen, unsubstituted phenyl or phenyl bearing one or two substituents independently selected from methyl, ethyl, methoxy, ethoxy, fluoro, chloro, bromo, iodo, cyano and trifluoromethyl.

A preferred value for $T^4$ is, for example, hydrogen, alkoxycarbonyl or alkenyloxycarbonyl.

A preferred value for $T^6$ is, for example, hydrogen.

A preferred value for $T^3$ and $T^4$ when together they form alkylene is, for example, trimethylene or tetramethylene.

A preferred value for Zb is, for example, 1H-tetrazol-5-yl and which is especially preferred when attached ortho to the group U.

A particularly preferred combination of values is, for example, when $T^1$ and $T^3$ are both alkyl, or when $T^1$ is alkyl and $T^3$ together with $T^4$ form alkylene.

Compounds disclosed in our said co-pending applications which are of special interest are: methyl 2,6-dimethyl-4-[(2'-(1H-tetrazol-5-yl)biphenyl-4-yl)methoxy]pyridine-3-carboxylate; 2-ethyl-5,6,7,8-tetrahydro-4-[(2'-(1H-tetrazol-5-yl)biphenyl-4-yl)methoxy]quinoline; 6,7-dihydro-2-methyl-4-[(2'-(1H-tetrazol-5-yl)biphenyl-4-yl)methoxy]-5H-cyclopenta[b]pyridine; methyl 2-ethyl-6-methyl-4-[(2'-(1H-tetrazol-5-yl)biphenyl-4-yl)methoxy]pyridine-3-carboxylate; methyl 6-ethyl-2-methyl-4-[(2'-(1H-tetrazol-5-yl)biphenyl-4-yl)methoxy]pyridine-3-carboxylate; methyl 2,6-diethyl-4-[(2'-(1H-tetrazol-5-yl)biphenyl-4-yl)methoxy]pyridine-3-carboxylate; 6,7-dihydro-2-ethyl-4-[(2'-(1H-tetrazol-5-yl)biphenyl-4-yl)methoxy-5H-cyclopenta[b]pyridine; 2,6-dimethyl-3-phenyl-4-[(2'-(1H-tetrazol-5-yl)biphenyl-4-yl)methoxy]pyridine; and allyl 2,6-dimethyl-4-[(2'-(1H-tetrazol-5-yl)biphenyl-4-yl)methoxy]pyridine-3-carboxylate; together with their non-toxic salts.

In the above-mentioned published European patent applications, the compounds of the formula I and II defined therein include racemic and optically active forms which possess the useful pharmacological properties described therein where one or more chiral centres are present. In addition generic terms such as "alkyl" include both straight and branched chain variants when the carbon numbers permit. However, when a particular radical such as "propyl" is given, it is specific to the straight chain variant, branched chain variants such as "isopropyl" being specifically named where intended. The same convention applies to other radicals.

In European Patent Application, Publication No. 253310 there are described imidazole derivatives of the formula III (set out hereinafter) wherein Alk. is a (3–10C)alkyl group, $X^1$ is selected from hydrogen, fluoro, chloro, bromo, iodo, nitro, trifluoromethyl and cyano; and $L^1$ and $L^2$ are selected from hydrogen, fluoro, chloro, bromo, iodo, nitro, (1–4C)alkyl and (1–4C)alkoxy. These compounds are described therein as possessing AII antagonist properties.

We have now discovered that the boron compounds of the present invention provide a convenient means for obtaining quinoline derivatives of the formula I or pyridine derivatives of the formula II wherein X and U are optionally substituted p-phenylene and Za and Zb are tetrazolyl, or imidazole derivatives of the formula III, wherein the other variables have any of the values defined hereinbefore.

According to the invention there is provided a boron compound of the formula IV (set out hereinafter) wherein Q is selected from a 4-quinolyloxy moiety of the formula Va (set out hereinafter) wherein $R^1$, $R^2$, $R^3$, $R^4$ and Ra have any of the meanings defined hereinbefore, a 4-pyridyloxy moiety of the formula Vb (set out hereinafter) wherein $T^1$, $T^2$, $T^3$ and $T^4$ have any of the meanings defined hereinbefore and a 1-imidazolyl moiety of the formula Vc (set out hereinafter) wherein Alk. and $X^1$ have any of the meanings defined hereinbefore;

$Y^1$ is selected from hydrogen, (1–4C)alkyl, (1–4C)alkoxy, halogeno, (1–4C)alkanoyl, trifluoromethyl, cyano and nitro; and $G^1$ and $G^2$ are independently selected from a hydroxy, (1–4C)alkoxy, (1–6C)alkyl and phenyl group, the latter optionally substituted by an (1–4C)alkyl, (1–4C)alkoxy or halogeno group; or $G^1$ together with $G^2$ forms an (1–4C)alkylenedioxy group attached to the boron atom, a methylene group of which may optionally bear 1 or 2 (1–4C)alkyl groups; or $G^1$ and $G^2$ together with the boron atom to which they are attached complete a 4- or 6-membered ring of alternate boron and oxygen atoms wherein each boron atom of the ring bears an identical group of the formula VI (set out hereinafter) wherein Q and $Y^1$ have any of the meanings defined above; or an acid or base addition salt thereof.

It will be appreciated that the letter B used in formula IV (and in any other formulae referred to herein) is the chemical symbol for boron.

A particular value for Q when it is a 4-quinolyloxy moiety of formula Va includes, for example, when it has any of the following values: -2-methyl-4-quinolyloxy, 2-ethyl-4-quinolyloxy, 2-ethyl-6-methoxy-4-quinolyloxy, 6,7-dimethoxy-2-ethyl-4-quinolyloxy, 2-ethyl-5,6,7-trimethoxy-4-quinolyloxy, 2-ethyl-6-hydroxy-4-quinolyloxy, 2-ethyl-6-methylthio-4-quinolyloxy, 2-ethyl-7-hydroxymethyl-4-quinolyloxy, 2-ethyl-6-(2-fluoroethoxy)-4-quinolyloxy, 2-ethyl-6-carboxamido-4-quinolyloxy, 2-ethyl-6-fluoro-4-quinolyloxy, 2-ethyl-6-isopropoxy-4-quinolyloxy or 6-aminomethyl-2-ethyl-4-quinolyloxy.

A particularly suitable value for $R^1$ is, for example, when it is (1-4C)alkyl, for example, methyl, ethyl or propyl, of which methyl and ethyl are preferred.

A particularly suitable value for $R^2$, $R^3$, $R^4$ or Ra is, for example, hydrogen.

A particular value for Q when it is a 4-pyridyloxy moiety of formula Vb includes, for example, when it is a 2,6-dimethyl-3-methoxycarbonyl-4-pyridyloxy, 2-ethyl-5,6,7,8-tetrahydro-4-quinolyloxy, 6,7-dihydro-2-methyl-5H-cyclopenta[b]pyrid-4-yloxy, 2-ethyl-6-methyl-3-methoxycarbonyl-4-pyridyloxy, 6-ethyl-2-methyl-3-methoxycarbonyl-4-pyridyloxy, 2,6-dimethyl-3-methoxycarbonyl-4-pyridyloxy, 6,7-dihydro-2-ethyl-5H-cyclopenta[b]pyrid-4-yloxy, 2,6-dimethyl-3-phenyl-4-pyridyloxy or 2,6-dimethyl-3-allyloxycarbonyl-4-pyridyloxy moiety.

Particularly suitable values for $T^1$, $T^2$, $T^3$ or $T^4$, or $T^3$ and $T^4$ together, are those preferred values and particularly preferred combinations of values given above.

A particular value for Q when it is a 1-imidazolyl moiety of the formula Vc includes, for example, when it is a 2-butyl-4-chloro-5-hydroxymethyl-1-imidazolyl moiety.

A particularly suitable value for Alk. is, for example, propyl or butyl; and for $X^1$ is, for example, chloro.

A particular value for $Y^1$ or for an optional substituent on $G^1$ or $G^2$ when it is phenyl is, for example, when it is alkyl: methyl or ethyl; when it is alkoxy: methoxy or ethoxy; and when it is halogeno: fluoro, chloro or bromo.

A particular value for $Y^1$ when it is alkanoyl is, for example, formyl, acetyl or propioyl.

A particular value for $G^1$ or $G^2$ includes, for example, when it is alkoxy: methoxy or ethoxy; and when it is alkyl: methyl, ethyl, propyl, isopropyl, butyl or tert-butyl.

A particular value for $G^1$ and $G^2$ when together they form an alkylenedioxy group in which a methylene group may optionally bear 1 or 2 alkyl groups is, for example, a group of the formula $-O.CH_2.O-$, $-O.CH_2.CH_2.O-$, $-O.CH_2.CH_2.CH_2.O-$ or $-O.CH_2.C(CH_3)_2.CH_2.O-$.

A preferred value for Q is when it is a 4-quinolyloxy moiety of formula Va, for example, 2-ethyl-4-quinolyloxy, or when it is a 4-pyridyloxy moiety of formula Vb, for example, 2-ethyl-5,6,7,8-tetrahydro-4-quinolyloxy.

A preferred value for $Y^1$ is, for example, hydrogen.

A preferred value for $G^1$ and $G^2$ includes, for example, when they are both hydroxy, or when $G^1$ and $G^2$ together form an alkylenedioxy group as defined above, for example the group $-O.CH_2.C(CH_3)_2.CH_2.O-$.

Compounds of the invention which are of particular interest include, for example, those compounds of formula IV described hereinafter in the accompanying Examples 1 to 4, and these compounds, and the acid or base addition salts thereof, are provided as a further feature of the invention.

The compounds of the formula IV may be obtained by standard procedures of organic chemistry well known in the art for the production of structurally analogous compounds. Such procedures are provided as a further feature of the invention and include, by way of example, the following procedures in which the generic radicals have any of the values given above, unless otherwise stated:

a) A compound of the formula VIIIa wherein $R^1$ is other than hydrogen, a compound of the formula VIIIb wherein $T^1$ and $T^3$ are other than hydrogen, or a compound of the formula VIIIc is alkylated with a compound of the formula VII wherein Hal. stands for a suitable leaving group such as chloro, bromo, iodo, methanesulphonyloxy or p-toluenesulphonyloxy.

The alkylation is generally carried out in the presence of a suitable base, for example, an alkali metal alkoxide such as sodium methoxide or sodium ethoxide, an alkali metal carbonate such as sodium carbonate or potassium carbonate, or an alkali metal hydride such as sodium hydride and in a solvent or diluent, for example, a (1-4C)alkanol such as methanol or ethanol when an alkali metal alkoxide is used, or in a polar solvent such as N,N-dimethylformamide or N-methylpyrrolidone and at a temperature in the range, for example, 10°-100° C. Alternatively, a quaternary ammonium hydroxide may be used in a mixture of an aqueous or non-aqueous solvent such as water and dichloromethane.

Certain compounds of the formula VIIIa, VIIIb and VIIIc are already known and others may be obtained by analogy therewith using standard procedures of organic chemistry well known in the art, for example as described in standard works of heterocyclic chemistry such as that edited by Elderfield, or in Org. Syn. 1951., Coll. Vol. III, pages 374 and 593; *Monatshefte fur Chemie.*, 1969, 100, 132; J. Chem. Soc. (B), 1968, 866; *Liebigs. Ann. Chem.*, 1982, 1656; *Heterocycles*, 1982, 13, 239; or in European Patent Application, Publication Nos. 412848, 453210 and 253310. The compounds of the formula VII may be obtained, for example, by heating at reflux a 4-methylphenylboronic acid in a suitable solvent such as methyl chloroform with azeotropic removal of water, followed by radical bromination (which may be carried out in situ), for example with bromine or N-bromosuccinimide and azo(-bisisobutyronitrile). Alternatively, they may be obtained, for example, by heating together a 4-methylphenylboronic acid and the appropriate alkanediol (for example 2,2-dimethylpropan-1,3-diol) in a solvent such as cyclohexane at reflux with azeotropic removal of water, followed by a similar radical bromination procedure. If required, a compound of the formula VII wherein $G^1$ and $G^2$ are both hydroxy may be obtained by subsequent acid hydrolysis.

b) For a compound of formula IV wherein Q is a 4-quinolyloxy moiety of the formula Va or a 4-pyridyloxy moiety of the formula Vb, a compound of the formula Xa or Xb wherein $P^2$ is a suitable leaving group (such as chloro, bromo, iodo, methanesulphonyloxy, p-toluenesulphonyloxy or trifluoromethanesulphonyloxy) is reacted with an alcohol of the formula IX.

The reaction is generally carried out in the presence of a suitable base, for example an alkali metal alkoxide such as sodium methoxide or ethoxide or an alkali metal hydride such as sodium hydride and in a suitable solvent or diluent, for example a (1-4C)alkanol such as methanol or ethanol when an alkali metal alkoxide is used, or a polar solvent such as N,N-dimethylformamide. Alternatively, an alcohol of the formula IX may be used in the form of its preformed alkali metal salt or di-alkali metal salt (when $G^1$ and/or $G^2$ is hydroxy). The reaction is usually performed at a temperature in the range of 40° to 120° C. The reaction may alternatively be carried out with a formula IX compound in the presence of an acid catalyst such as p-toluenesulphonic acid, instead of under basic conditions, and in the presence of an inert solvent or diluent such as toluene.

The compounds of the formula Xa and Xb may be obtained, for example, by halogenation of the corresponding compound of formula VIIIa or VIIIb, for example, by reaction with phosphorus oxychloride in the absence of a solvent, or in the presence of an inert solvent or diluent such as toluene or dioxane, and at a temperature in the range 60°–110° C. Compounds of the formula Xa or Xb wherein $P^2$ is methanesulphonyloxy, p-toluenesulphonyloxy or trifluoromethanesulphonyloxy and $R^1$, $T^1$ and $T^3$ are other than hydrogen may be obtained, for example, by acylation of the corresponding compounds of formula VIIIa or VIIIb with the corresponding sulphonyl chloride under standard conditions. Compounds of the formula Xa or Xb wherein $P^2$ is methanesulphonyl may be obtained from alkylation of the corresponding mercaptoquinolines or mercaptopyridines followed by oxidation under standard conditions. The alcohols of the formula IX may be obtained from a compound of the formula VII, for example, by reaction with potassium acetate and hexaoxacyclooctadecane in dimethoxyethane at reflux, followed by reaction of the resultant acetoxy compound with lithium borohydride in tetrahydrofuran at a temperature in the range of 0°–25° C.

Whereafter, those compounds of the formula IV wherein $G^1$ and $G^2$ are both hydroxy may be obtained by acid hydrolysis of a compound of the formula IV wherein $G^1$ and/or $G^2$ is other than hydroxy. It will be appreciated that this acidic hydrolysis may be carried out in situ after carrying out procedure (a) or (b).

Whereafter, when a salt of a compound of formula IV is required, it may be obtained, for example, by reaction with the appropriate acid or base, or by any other conventional salt formation procedure.

Certain of the intermediates defined herein are novel, for example, certain compounds of the formula VII, and these are provided as a further feature of the invention.

Further aspects of the invention are that it provides novel and convenient processes for the preparation of certain quinoline derivatives of the formula I or pyridine derivatives of the formula II wherein X and U are optionally substituted p-phenylene and Za and Zb are tetrazolyl, or imidazole derivatives of the formula III, and wherein the other variables have any of the meanings defined above.

Thus, according to a further aspect of the invention there is provided a process for the manufacture of a compound of the formula XI (set out hereinafter) wherein Q is selected from a 4-quinolyloxy moiety of the formula Va, a 4-pyridyloxy moiety of the formula Vb and a 1-imidazolyl moiety of the formula Vc;

$Y^1$ is selected from hydrogen, (1–4C)alkyl, (1–4C)alkoxy, halogeno, (1–4C)alkanoyl, trifluoromethyl, cyano and nitro; $Y^2$ is selected from hydrogen, (1–4C)alkyl, (1–4C)alkoxy, halogeno, trifluoromethyl, cyano and nitro;

and wherein $R^1$, $R^2$, $R^3$, $R^4$, Ra, $T^1$, $T^2$, $T^3$, $T^4$, $X^1$ and Alk. have any of the meanings defined above; which comprises:

(i) Reaction of a compound of the formula IV wherein Q, $Y^1$, $G^1$ and $G^2$ have any of the meanings defined above with a compound of the formula XII wherein $P^1$ is an electron-deficient phenyl group or is a pyridyl or pyrimidyl group; W is a bromo, iodo or trifluoromethanesulphonyloxy group; and $Y^2$ is hydrogen, (1–4C)alkyl, (1–4C)alkoxy, halogeno, trifluoromethyl, cyano or nitro; in the presence of a catalyst selected from palladium(O), palladium(II), nickel(O) and nickel(II), optionally in the presence of a radical initiator; and optionally in the presence of lithium chloride; to give a compound of the formula XIII wherein Q, $Y^1$, $Y^2$ and $P^1$ have any of the values defined above; followed by (ii) Reaction of a compound of the formula XIII as defined above with a base selected from an alkali metal hydroxide, (1–12C)alkanoate, (1–12C)alkanethiolate, phenolate, thiophenolate and diphenylphosphide, wherein any phenyl ring of the latter three groups may optionally bear a (1–4C)alkyl, (1–4C)alkoxy or halogeno group.

In step (i), a particular value for $P^1$ when it is an electron-deficient phenyl group includes, for example, a phenyl group bearing 1, 2 or 3 electron-withdrawing groups independently selected from halogeno (typically chloro or bromo), nitro, cyano and trifluoromethyl. A preferred value for $P^1$ is, for example, a nitrophenyl group or a 4-pyridyl, 4-cyanophenyl, (4-cyano-3-trifluoromethyl)phenyl, 4-(di(1–4C)alkylaminosulphonyl)phenyl or 4-((1–4C)alkylsulphonyl)phenyl group, of which 4-nitrophenyl is especially preferred. A preferred value for W is, for example, bromo. Particular and preferred values for Q, $Y^1$, $G^1$ or $G^2$, or for $G^1$ and $G^2$ together, are those given above. Particular values for $Y^2$ when it is alkyl, alkoxy or halogeno are, for example, those given above for $Y^1$, a preferred value for $Y^2$ being, for example, hydrogen. A preferred catalyst is, for example, tetrakis(triphenylphosphine)palladium or palladium(II)chloride, especially the latter. A preferred radical initiator is, for example, azo(-bisisobutyronitrile).

Step (i) is preferably carried out in the presence of a base, such as sodium or potassium carbonate or triethylamine. Step (i) is also preferably carried out in an inert solvent or diluent, for example, a hydrocarbon such as toluene or xylene, an ether, such as dioxan or tetrahydrofuran, an (1–4C)alkanol such as methanol, ethanol or butanol, water, or mixture thereof, for example a mixture of water, methanol and toluene or butanol and water, and at a temperature in the range of, for example, 50° C. to 150° C., and conveniently at or about the reflux temperature of the solvent or mixture of solvents used.

In step (ii), suitable bases are, by way of example: for an alkali metal hydroxide: sodium or potassium hydroxide; for an alkali metal alkanolate: an alkali metal (1–8C)alkanolate, for example an alkali metal (1–4C)alkoxide, such as sodium or potassium methoxide, ethoxide, propoxide or butoxide;

for an alkali metal alkanethiolate: an alkali metal (1–8C)alkanethiolate, for example an alkali metal (1–4C)alkanethiolate such as sodium or potassium methanethiolate, ethanethiolate, propanethiolate or butanethiolate;

for a phenolate or thiophenolate: the sodium or potassium salt of phenol, thiophenol or a phenol or thiophenol bearing a methyl, ethyl, methoxy, ethoxy, fluoro, chloro, bromo or iodo group, for example a 4-halogenothiophenol such as 4-fluorothiophenol. A particularly preferred base is sodium or potassium propanethiolate, methoxide or ethoxide.

It will be appreciated that when the base is an alkali metal alkanolate, alkanethiolate, phenolate, thiophenolate or diphenylphosphide, it may be generated in situ from the corresponding alkanol, alkanethiol, phenol, thiophenol or diphenylphosphine with a suitable alkali metal base such as an alkali metal hydride, for example, lithium, potassium or sodium hydride. Conveniently, a solution of an alkali metal alkanolate in the corresponding alcohol can be used, such as a solution of sodium methoxide in methanol.

The reaction is conveniently carried out in a suitable inert organic solvent or diluent, for example, a polar solvent such as N,N-dimethylformamide or N-methylpyrrolidone. Alternatively, or in admixture, an alkanol such as methanol or ethanol may be used, for example, when an alkali metal hydroxide or alkoxide such as sodium or potassium hydroxide, methoxide or ethoxide is employed. The reaction is generally carried out at a temperature in the range, for example, $-30°$ C. to $50°$ C. It will be appreciated that the choice of temperature will depend on the nature of the base employed. For example, when an alkali metal alkanethiolate or alkanolate is used, a temperature in the range of $0°$ C. to ambient temperature is preferred.

The compounds of the formula XII used in step (i) may be obtained, for example, as illustrated in Scheme 1.

It will be appreciated that an alternative process variant for step (i) involves the use of a starting material of formula XII in which the group $P^1$ is attached to a nitrogen atom of the tetrazole ring other than at the 1-position. The product so obtained is then reacted with a base according to step (ii). The necessary starting materials for such a variant may be obtained by methods well known in the art for the preparation of structurally analogous compounds.

According to a further aspect of the invention there is provided a process for the manufacture of a compound of the formula XI (set out hereinafter) wherein Q is selected from a 4-quinolyloxy moiety of the formula Va, a 4-pyridyloxy moiety of the formula Vb and a 1-imidazolyl moiety of the formula Vc;

$Y^1$ is selected from hydrogen, (1–4C)alkyl, (1–4C)alkoxy, halogeno, (1–4C)alkanoyl, trifluoromethyl, cyano and nitro; $Y^2$ is selected from hydrogen, (1–4C)alkyl, (1–4C)alkoxy, halogeno, trifluoromethyl, cyano and nitro;

and wherein $R^1$, $R^2$, $R^3$, $R^4$, Ra, $T^1$, $T^2$, $T^3$, $T^4$, $X^1$ and Alk. have any of the meanings defined above; which comprises:

(1) Reaction of a compound of the formula IV wherein Q, $Y^1$, $G^1$ and $G^2$ have any of the meanings defined above with a compound of the formula XIV wherein $W^1$ is a bromo, iodo or trifluoromethanesulphonyloxy group; and $Y^2$ has any of the meanings defined above; in the presence of a catalyst selected from palladium(0), palladium (II), nickel(0) and nickel(II), optionally in the presence of a radical initiator; and optionally in the presence of lithium chloride; to give a compound of the formula XV wherein Q, $Y^1$ and $Y^2$ have any of the values defined above; followed by (2) Reaction of a compound of the formula XV as defined above with a trisubstituted tin azide of the formula $(Rx)_3.Sn.N_3$ wherein Rx is a (1–6C)alkyl or phenyl group, the latter optionally substituted by an (1–4C)alkyl, (1–4C)alkoxy or halogeno group; to give a compound of the formula XVI wherein Q, $Y^1$, $Y^2$ and Rx have any of the meanings defined above; followed by (3) Removal of the trisubstituted tin moiety from the compound of formula XVI.

In step (1), $W^1$ is preferably bromo and the particular and preferred values for Q, $Y^1$, $Y^2$, $G^1$, $G^2$, or $G^1$ and $G^2$ together, a catalyst or a radical initiator are as defined for step (i) above. Step (1) is carried out in a similar manner to step (i) above.

In step (2), Rx is preferably alkyl, in particular, for example, (1–4C)alkyl such as methyl or butyl, of which the latter is especially preferred. Step (2) is conveniently carried out in a suitable solvent or diluent, such as toluene or xylene, and at a temperature in the range, for example, $50°-150°$ C., and conveniently at the reflux temperature of the solvent used.

In step (3), the trisubstituted tin moiety $Sn(Rx)_3$ may be removed, for example, by acid or base hydrolysis. The reaction is conveniently carried out, for example, by treatment of the compound of formula XVI with mineral acid, such as aqueous hydrochloric acid, in the presence of a suitable solvent or diluent. A suitable solvent or diluent is, for example, a hydrocarbon such as toluene or xylene, an ether such as dioxan or tetrahydrofuran, or water, or mixtures thereof. The reaction is generally carried out at a temperature in the range, for example, $0°-50°$ C., and conveniently at or about ambient temperature.

The compounds of the formula XIV used in step (1) and the trisubstituted tin azide of the formula $(Rx)_3.Sn.N_3$ used in step (3) are known or can be made by standard procedures of organic chemistry well known in the art.

In a modified procedure for carrying out process steps (2) and (3), a compound of the formula XVI is generated in situ from a compound of the formula XV by reaction with an azide of the formula $(Rx)_3.Sn.N_3$. The trisubstituted tin moiety $Sn(Rx)_3$ may then be removed without isolation of the compound of the formula XVI, for example, by addition of aqueous mineral acid to the reaction mixture.

Whereafter carrying out steps (i) and (ii) or steps (1), (2) and (3), when a non-toxic salt of a compound of formula XI is required, it may be obtained, for example, by reaction with the appropriate base affording a physiologically acceptable cation, or with the appropriate acid affording a physiologically acceptable anion, or by any other conventional salt formation procedure.

Further, when an optically active form of a compound of formula XI is required, the aforesaid processes may be carried out using an optically active starting material. Alternatively, the racemic form of a compound of formula XI may be resolved, for example by reaction with an optically active form of a suitable organic base, for example, ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula XI may be liberated by treatment with acid using a conventional procedure, for example using an aqueous mineral acid such as dilute hydrochloric acid.

The process comprising steps (i) and (ii) and the process comprising steps (1), (2) and (3) are particularly suitable for the manufacture of compounds of the formula XI wherein Q is a 4-quinolyloxy or 4-pyridyloxy group as defined above, and especially when the tetrazole group of the formula XI compound is at the ortho position relative to the adjacent phenyl group. In particular, the processes are especially useful for the preparation of those compounds described in our copending applications as being particularly preferred or of special interest. Specific embodiments of the process comprising steps (i) and (ii) and of the process comprising steps (1), (2) and (3) which are of special interest include, for example, those set out hereinafter in the accompanying Examples, and these are provided as a further feature of the invention.

The antagonism of one or more of the physiological actions of AII and, in particular, the antagonism of the interaction of AII with the receptors which mediate its effects on a target tissue, may be assessed using one or more of the following, routine laboratory procedures:

Test A

This in vitro procedure involves the incubation of the test compound initially at a concentration of 100 micromolar (or less) in a buffered mixture containing fixed concentrations of radiolabelled AII and a cell surface membrane fraction prepared from a suitable angiotensin target tissue. In this test, the source of cell surface membranes is the guinea pig adrenal gland which is well known to respond to AII. Interaction of the radiolabelled AII with its receptors (assessed as radiolabel bound to the particulate membrane fraction following removal of unbound radiolabel by a rapid filtration procedure such as is standard in such studies) is antagonized by compounds which also bind to the membrane receptor sites and the degree of antagonism (observed in the test as displacement of membrane-bound radioactivity) is determined readily by comparing the receptor-bound radioactivity in the presence of the test compound at the specified test concentration with a control value determined in the absence of the test compound. Using this procedure compounds showing at least 50% displacement of radiolabelled AII binding at a concentration of $10^{-4}$M are retested at lower concentrations to determine their potency. For determination of the $IC_{50}$ (concentration for 50% displacement of radiolabelled AII binding), concentrations of the test compound are ordinarily chosen to allow testing over at least four orders of magnitude centred about the predicted approximate $IC_{50}$, which latter is subsequently determined from a plot of percentage displacement against concentration of the test compound.

In general, compounds of formula I or II as defined above show significant inhibition in Test A at a concentration of 50 micromolar or much less.

Test B

This in vitro test involves the measurement of the antagonistic effects of the test compound against ZII-induced contractions of isolated rabbit aorta, maintained in a physiological salt solution at 37° C. In order to ensure that the effect of the compound is specific to antagonism of AII, the effect of the test compound on noradrenaline-induced contractions may also be determined in the same preparation.

In general, compounds of formula I or II as defined above show significant inhibition in Test B at a final concentration of 50 micromolar or much less.

Test C

This in vivo test involves using terminally-anaesthetised or conscious rats in which an arterial catheter has been implanted under anaesthesia for the measurement of changes in blood pressure. The AII antagonistic effects of the test compound following oral or parenteral administration, are assessed against angiotensin II-induced pressor responses. To ensure that the effect is specific, the effect of the test compound on vasopressin-induced pressor responses may also be determined in the same preparation.

The compounds of formula I or II as defined above generally show specific AII-antagonist properties in Test C at a dose of 50 mg/kg body weight or much less, without any overt toxicological or other untoward pharmacological effect.

Test D

This in vivo test involves the stimulation of endogenous AII biosynthesis in a variety of species including rat, marmoset and dog by introducing a diet of low sodium content and giving appropriate daily doses of a saluretic known as frusemide. The test compound is then administered orally or parenterally to the animal in which an arterial catheter has been implanted under anaesthesia for the measurement of changes in blood pressure.

In general compounds of formula I or II as defined above will show AII-antagonist properties in Test D as demonstrated by a significant reduction in blood pressure at a dose of 50 mg/kg body weight or much less, without any overt toxicological or other untoward pharmacological effect.

By way of illustration of the angiotensin II inhibitory properties of compounds of formula I and II, 2-methyl-4-[(2'-(1H-tetrazol-5-yl)biphenyl-4-yl)methoxy]quinoline hydrochloride gave the following results in tests A, B and C described above:

In test A: an average $IC_{50}$ of $1.7 \times 10^{-8}$M;

In test B an average $pA_2$ of 8.95;

In test C: $ED_{50}$ of 0.5 mg/kg (i.v. administration).

Similarly, 2-methyl-5,6,7,8-tetrahydro-4-[(2'-(1H-tetrazol-5-yl)methoxy]quinoline hydrochloride gave the following results in tests A and C described above:

In test A: $IC_{50}$ of $3 \times 10^{-8}$M;

In test C: $ED_{50}$ of 0.28 mg/kg (i.v. administration).

The invention will now be illustrated by the following non-limiting Example in which, unless otherwise stated:

(i) concentrations and evaporations were carried out by rotary evaporation in vacuo;

(ii) operations were carried out at room temperature, that is in the range 18°–26° C.;

(iii) yields, where given, are intended for the assistance of the reader only and are not necessarily the maximum attainable by diligent process development;

(iv) $^1$H NMR spectra were normally determined at 270 MHz in CDCl$_3$ using tetramethylsilane (TMS) as an internal standard, and are expressed as chemical shifts (delta values) in parts per million relative to TMS using conventional abbreviations for designation of major peaks: s, singlet; m, multplet; t, triplet; br, broad; d, doublet; and (v) the term "1H-tetrazol-5-yl" stands for "1H-1,2,3,4-tetrazol-5-yl".

EXAMPLES 1–4

These Examples illustrate the production of a boron compound of the formula IV.

EXAMPLE 1

A solution of 2-ethyl-4-quinolone (6.9 g; 0.04 mole), (prepared using a similar procedure to that described in Org. Syn., Coll., Vol. III, p. 374 and p. 593 from aniline and ethyl propionylacetate) in (NMP) (50 ml) was added over 30 minutes to a stirred suspension of sodium hydride (1.6 g of a 60% dispersion in mineral oil; 0.04 mole) in NMP (50 ml) and the mixture stirred for 30 minutes. A solution of 2-(4-bromomethylphenyl)-5,5-dimethyl-1,3,2-dioxaborinane in cyclohexane [previously prepared by heating a mixture of 4-methylphenylboronic acid (6.8 g) and 2,2-dimethylpropan-1,3-diol (5.2 g) in cyclohexane (150 ml) at reflux with azeotropic removal of water, followed by the addition of N-bromosuccinimide (8.9 g) and azo(bisisobutyronitrile) (0.2 g), heating the mixture at reflux for 3 hours, and removing suspended succinimide by filtration] was added and the mixture was heated at 60°-70° C. for 18 hours. The mixture was allowed to cool and acetic acid was then added until the mixture was at pH 4, followed by water (200 ml) and ethyl acetate (200 ml). The mixture was stirred for 20 minutes and then the organic phase was separated, washed with water and dried (MgSO$_4$). Volatile material was removed by evaporation to give a crystalline solid. The solid was dissolved in ethyl acetate (150 ml), concentrated hydrochloric acid (3 ml) and water (3 ml) were added and the mixture was stirred for 18 hours. The resultant precipitate was collected by filtration, washed with ethyl acetate and dried to give 4-[(2-ethylquinolin-4-yloxy)methyl]-phenylboronic acid hydrochloride (7 g) as a solid; NMR (d$_4$-methanol): 1.5(t,3H), 3.21(q,2H), 5.78(s,2H), 7.55(s,1H), 7.6-8.15(m,7H), 8.40(d,2H).

EXAMPLE 2

A mixture of 2-ethyl-4-quinolone (1.0 g), the anhydride of 4-bromomethylphenylboronic acid (compound A), (2.7 g) potassium carbonate (2.0 g) and NMP (5 ml) was heated at 70° C. for 3 hours with stirring. The mixture was allowed to cool and then added slowly to water (50 ml) with vigorous stirring. The mixture was allowed to stand for 20 minutes and then the solid precipitate collected by filtration. The solid was suspended in ethyl acetate (25 ml), concentrated hydrochloric acid (2 ml) was added, and the mixture was then stirred for 30 minutes. Water (10 ml) was added and the mixture allowed to stand for a further 20 minutes. The suspended solid was collected by filtration and washed with ethyl acetate (10 ml) to give 4-[(2-ethylquinolin-4-yloxy)methyl]phenylboronic acid hydrochloride (1.2 g); NMR similar to that obtained for the product of Example 1.

Compound A was obtained as follows:

A mixture of 4-methylphenylboronic acid (27.2 g; 0.2 mole) in methyl chloroform (250 ml) was heated at reflux with azeotropic removal of water until approximately 2.5 ml of water was collected and a crystalline slurry was formed. A solution of azo(bisisobutyronitrile) (1.0 g) and bromine (32 g) in methyl chloroform (25 ml) was added to the refluxing slurry over 2-3 hours. The mixture was then refluxed until the bromine colour was discharged. The reaction mixture was allowed to cool and stirred at 10°-15° C. for 30 minutes. The suspended solid was collected by filtration, washed with methyl chloroform (2×50 ml) and dried at ambient temperature to give the anhydride of 4-bromomethylphenylboronic acid (29 g) (Compound A) as a white, crystalline solid.

EXAMPLE 3

A mixture of 4-methylphenylboronic acid (34.0 g; 0.25 mole) and 2,2-dimethylpropan-1,3-diol (26.0 g; 0.25 mole) was heated in cyclohexane (500 ml) at reflux with azeotropic removal of water. When no further water collected, N-bromosuccinimide (44.5 g) and azo(bisisobutyronitrile) (1.0 g) was added and the mixture was heated at reflux for 3 hours. Suspended succinimide was removed by filtration and the cooled filtrate was added to a mixture of 2-ethyl-4-quinolone (31.2 g; 0.18 mole), potassium carbonate (38.4 g; 0.21 mole) and NMP (120 ml). The mixture was heated at 60°-70° C. for 18 hours and then allowed to cool. Aqueous potassium carbonate solution (10% w/v; 400 ml) was added and the resulting crystalline precipitate collected by filtration, washed with water and cyclohexane and dried at ambient temperature. There was thus obtained 2-(4-[(2-ethylquinolin-4-yloxy)methyl]phenyl)-5,5-dimethyl-1,3,2-dioxaborinane (37 g), m.p. 154°-156° C.; NMR(CDCl$_3$): 1.03(6H, s), 1.37(3H, t), 2.94(2H, q), 3.80(4H, s), 5.30(2H, s), 6.72(1H, s), 7.4-8.3(8H, m).

EXAMPLE 4

Sodium hydride (60% dispersion in oil; 180 mg) was added to a mixture of 2-ethyl-5,6,7,8-tetrahydro-4(1H)-quinolone (660 mg) and 4-bromomethylphenylboronic acid (800 mg) (obtained as described in J. Amer. Chem. Soc. 1958, 80, 835) in DMF (12 ml) under an atmosphere of argon. The mixture was stirred for 40 hours and then water (0.2 ml) was added. Volatile material was removed by evaporation and the residue was dissolved in warm 0.5M sodium hydroxide solution (10 ml). Insoluble material was removed by filtration and the filtrate was acidified to pH 4 with 20% citric acid solution. The precipitate solid was collected by filtration, washed with water (20 ml) and dried under high vacuum to give 4-[(2-ethyl-5,6,7,8-tetrahydroquinolin-4-yl)oxymethyl]phenylboronic acid (C) (1.15 g), m.p. 229°-231° C.; NMR (d$_6$-DMSO): 1.3(t,3H), 1.6-1.9(m,4H), 2.5-2.7(m,2H), 2.75-2.95(m,4H), 5.4(s,2H), 7.3(d,2H), 7.4(s,1H, 7.5(d,2H).

The starting material 2-ethyl-5,6,7,8-tetrahydro-4(1H)-quinolone [m.p. 226°-227° C.; NMR (d$_6$-DMSO): 1.55-1.75(m,4H), 2.25(t,2H), 2.4 (q,2H), 2.45-2.55(m,2H), 5.8(s,1H)] was obtained using an analogous procedure to that described for the preparation of 2-methyl-5,6,7,8-tetrahydro-4(1H)-quinolone in Liebigs Ann. Chem., 1982, 1656-1676 but reducing the intermediate 2-ethyl-4(1H)-quinolone by catalytic hydrogenation over platinum oxide in acetic acid at one atmosphere pressure.

EXAMPLES 5-9

These examples illustrate the production of a compound of the formula XIII from a compound of formula IV.

EXAMPLE 5

A mixture of potassium carbonate (5.8 g), 5-(2-bromophenyl)-1-(4-nitrophenyl)-1H-tetrazole (5.81 g) (Compound B), water (43 ml), toluene (43 ml), and methanol (43 ml) was heated to 60° C. to give a clear solution. 4-[(2-Ethylquinolin-4-yloxy)methyl]phenylboronic acid hydrochloride (4.3 g) and tetrakis(triphenylphosphine)palladium (0.032 g) were added and the reaction mixture heated at reflux for 4 hours. The mixture was allowed to cool and further toluene (50 ml) added. The organic phase was separated and the aqueous phase extracted with toluene (2×50 ml). The combined organic phases were evaporated and the resultant solid recrystallised from toluene to give 2-ethyl-4-[(2'-(1-(4- nitrophenyl)-1H-tetrazol-5-yl)biphenyl-4-yl)methoxy]-quinoline as a solid (4.3 g); NMR (CDCl$_3$): 1.42(3H,t), 3.0(2H,q), 5.23(2H,s), 6.67(2H,d), 6.75(1H,s), 6.85(2H,d), 7.25(2H,d), 7.43(1H,d), 7.55(1H,t), 7.70(3H,m), 7.90(3H,d), 8.05(1H,d), 8.20(1H,d).

The starting material B was obtained as follows:

(i) Thionyl chloride (120.5 g) was added to a stirred mixture of 2-bromobenzoic acid (194 g) in toluene (500 ml) and N,N-dimethylformamide (DMF) (5 ml) and the mixture heated at 80° C. for 4 hours. The solution was cooled to 20° C. and added slowly to a solution of 4-nitroaniline (133.1 g) in toluene (500 ml) and NMP (120 ml), maintaining the temperature of the reaction mixture between 20°-25° C. The reaction mixture was then stirred for 24 hours when a solid precipitated. Water (360 ml) was added with rigorous stirring and the suspended solid collected by filtration, and washed successively with water, toluene and acetonitrile to give 2-bromo-N-(4-nitrophenyl)benzamide as a solid, in 87% yield, which was used without further purification or characterisation.

(ii) Triethylamine (1.04 g; 10.38 mmol) was added to a mixture of 2-bromo-N-(4-nitrophenyl)benzamide (3 g; 9.35 mmol) in acetonitrile (12 ml) and DMF (0.189 g; 2.58 mmol) and the mixture was stirred for 90 minutes. Thionyl chloride (1.44 g; 12.14 mmol) was then added slowly keeping the reaction temperature below 25° C. The mixture was stirred for 5 hours at ambient temperature and then cooled to 10° C. Triethylamine (2.83 g; 28 mmol) was then added, followed by sodium azide (1.33 g; 20.4 mmol) and tetrabutylammonium bromide (0.42 g; 1.3 mmol). The mixture was stirred for 2 hours at 10° C. and then allowed to warm to ambient temperature and stirred for 24 hours. The mixture was poured into excess water and the precipitated solid collected by filtration. The solid was purified by trituration with a hot mixture of ethyl acetate (26 ml), hexane (2.6 ml) and triethylamine (0.1 ml) to give 5-(2-bromophenyl)-1-(4-nitrophenyl)-1H-tetrazole (B) (2.36 g; 73% yield) as an off-white solid; NMR (d$_6$-acetone; 270 MHz): 7.61-7.86(m, 6H), 8.41(d, 2H); microanalysis, found: C, 44.8; H, 2.1; N, 20.0; Br, 23.6%; C$_{13}$H$_8$BrN$_5$O$_2$ requires: C, 45.1; H, 2.3; N, 20.2; Br, 23.1%.

EXAMPLE 6

A mixture of potassium carbonate (1.08 g; 7.8 mmol), 5-(2-bromophenyl)-1-(4-nitrophenyl)-1H-tetrazole (1.16 g; 3.2 mmol) water (10 ml), toluene (10 ml), and methanol (10 ml) was heated to 60° C. to give a clear solution. 2-(4-[(2-Ethylquinolin-4-yloxy)-methyl]phenyl)-5,5-dimethyl-1,3,2-dioxaborinane (1.0 g; 2.6 mmol) and tetrakis(triphenylphosphine)palladium (0.06 g; 0.05 mmol) were added and the reaction mixture heated at reflux for 6 hours. The mixture was allowed to cool and further toluene (10 ml) added. The organic phase was separated and the aqueous phase extracted with toluene (2×20 ml). The combined organic phases were evaporated and the resultant solid recrystallised from toluene to give 2-ethyl-4-[(2'-(1-(4-nitrophenyl)-1H-tetrazol-5-yl)biphenyl-4-yl)methoxy]quinoline as a solid (0.8 g); m.p. and NMR similar to that of the product of Example 5.

EXAMPLE 7

Using an analogous procedure to that described in Example 18, but using 5-(2-bromophenyl)-1-(4-nitrophenyl)-1H-tetrazole (202 mg) in place of 2-bromobenzonitrile and proportionate quantities of the other necessary reagents, there was obtained after flash chromatography eluting with ethyl acetate/hexane (3:1 v/v) and trituration with ether/hexane, 2-ethyl-4-[(2'-(1-(4-nitrophenyl)-1H-tetrazol-5-yl)biphenyl-4-yl) methoxy]-5,6,7,8-tetrahydroquinoline (A) (134 mg) as an off white solid, m.p. 208°-210° C.; NMR (CDCl$_3$): 1.31(t,3H), 1.8-2.0(m,4H), 2.70(m,2H), 2.78(q,2H), 2.92(m,2H), 5.03(s,2H), 6.54(s,1H), 6.59(d,2H), 6.79(d,2H), 7.11(d,2H), 7.39(dd,1H), 7.67(m,2H), 7.85-7.95(m,3H); mass spectrum (+ve FAB DMSO, CH$_3$OH, NBA) 533 (M+H)$^+$; microanalysis, found: C,69.5; H,5.4; N,15.5; C$_{31}$H$_{28}$N$_6$O$_3$ requires: C,69.9; H,5.3; N,15.8%.

EXAMPLE 8

Using an analogous procedure to that described in Example 6, but starting from 5-(2-bromophenyl)-1-(4-cyano-3-trifluoromethyl)-1H-tetrazole (C) in place of Compound B, there was obtained 2-ethyl-4-[2'-(1-(4-cyano-3-trifluoromethylphenyl)-1H-tetrazol-5-yl)biphenyl-4-yl)methoxy]quinoline as a solid, m.p. 165°-6° C.

The starting material C was obtained using an analogous procedure to that described in Example 5, parts (i) and (ii) using 4-cyano-3-trifluoromethylaniline in place of 4-nitroaniline in part (i). The intermediates thus obtained were as follows:
2-bromo-N-(4-cyano-3-trifluoromethylphenyl)benzamide; m.p. 156°-160° C.
5-(2-bromophenyl)-1-(4-cyano-3-trifluoromethylphenyl)-1H-tetrazole; m.p. 177°-9° C.

EXAMPLE 9

Using an analogous procedure to that described in Example 5, but starting from 5-(2-bromophenyl)-1-(4-pyridyl)-1H-tetrazole (D) in place of compound B, there was obtained 2-ethyl-4-[(2'-(1-(4-pyridyl)-1H-tetrazol-5-yl)biphenyl-4-yl)methoxy]quinoline, m.p. 155°-170° C.

The starting material D was obtained using an analogous procedure to that described in Example 5, parts (i) and (ii) using 4-aminopyridine in place of 4-nitroaniline. The intermediates thus obtained were as follows:
2-bromo-N-(4-pyridyl)benzamide; m.p. 185°-6° C.
5-(2-bromophenyl)-1-(4-pyridyl)-1H-tetrazole; m.p. 121°-2° C.

EXAMPLE 10-16

These examples illustrate the production of a compound of the formula XI from a compound of formula XIII.

EXAMPLE 10

Sodium hydride (50% dispersion in mineral oil; 0.091 g; 1.9 mmol) was washed with hexane, dried with a stream of nitrogen and covered with N-methylpyrrolidone (NMP) (5 ml). The mixture was cooled to below 10° C. and propanethiol (0.145 g; 1.9 mmol) was added slowly with stirring. After 15 minutes, a solution of 2-ethyl-4-[(2'-(1-(4-nitrophenyl)-1H-tetrazol-5-yl)biphenyl-4-yl)methoxy]quinoline (0.5 g; 0.95 mmol) in NMP (10 ml) was added slowly maintaining the temperature of the reaction mixture below 10° C. The mixture was then stirred for 2 hours. Concentrated hydrochloric acid was added until the reaction mixture was pH2. Water (25 ml) was then added and the suspended white solid collected by filtration. The crude product was recrystallised from ethanol to give 2-ethyl-4-[(2'-(1H-tetrazol-5-yl)biphenyl-4-yl)methoxy]quinoline hydrochloride as a solid, in 64% yield; m.p. 178°-181° C.; NMR (d6-DMSO): 1.53(3H, t), 3.30(2H, q), 5.65(2H, s), 7.25(2H, d), 7.50-7.75(6H, m), 7.80(1H, t), 7.90(1H, s), 8.00(1H, t), 8.35(1H, d), 8.50(1H, d).

EXAMPLE 11

Using an analogous procedure to that described in Example 10, but using ethanol (95%; 0.092 g; 1.9 mmol) in place of propanethiol and stirring the reaction mixture for 4 hours, there was thus obtained 2-ethyl-4-[(2'-(1H-tetrazol-5-yl)biphenyl-4-yl)methoxy]quinoline hydrochloride as a solid, in 60% yield; m.p. and NMR similar to that obtained for the product of Example 10.

EXAMPLE 12

Using an analogous procedure to that described in Example 10, but using 2-ethyl-4-[(2'-(1-(4-nitrophenyl)-1H-tetrazol-5-yl)-biphenyl-4-yl)methoxy-5,6,7,8-tetrahydroquinoline (0.5 g) as starting material, there was obtained 2-ethyl-5,6,7,8-tetrahydro-4-[2'-(1H-tetrazol-5-yl)-biphenyl-4-yl)methoxy]quinoline hydrochloride as a solid, in 54% yield; m.p. 235°-237° C.; NMR similar to that obtained for the product of Example 20.

EXAMPLE 13

Using a similar procedure to that described in Example 12, but using sodium methoxide (2 equivalents) or sodium ethoxide (2 equivalents) in NMP in place of sodium hydride and propanethiol and carrying out the reaction at ambient temperature, there was obtained 2-ethyl-5,6,7,8-tetrahydro-4-[(2'-(1H -tetrazol-5-yl)biphenyl-4-yl)methoxy]quinoline hydrochloride in 80-90% yield; m.p. and NMR similar to that obtained for the product of Example 12.

EXAMPLE 14

Sodium methoxide (30 wt % solution in methanol; 7.2 ml) was added to a solution of 2-ethyl-4-[(2'-(1-(4-nitrophenyl)-1H-tetrazol-5-yl)biphenyl-4-yl)methoxy]quinoline (10 g) in NMP (30 ml) at 15°-20° C. and the solution was stirred for 4 hours. Methyl isobutyl ketone (30 ml) was added and the mixture was heated to 40° C. Concentrated hydrochloric acid (5.8 ml) was added dropwise maintaining the temperature at 40°-45° C. Water (60 ml) was then added and the mixture was stirred for 15 minutes at 40° C. The mixture was cooled to ambient temperature and the suspended solid collected by filtration. The solid was washed with water (2×8 ml), followed by ethanol (2×8 ml), and then dried under vacuum at 30° C. There was thus obtained 2-ethyl-4-[(2'-(1H)-tetrazol-5-yl)biphenyl-4-yl)methoxy]quinoline hydrochloride as a solid* , in 74% yield.
[*Recrystallisation from ethanol gives a product with m.p. and NMR similar to that obtained for the product of Example 10].

EXAMPLES 15 and 16

Using a similar procedure to that described in Example 14, but starting from 2-ethyl-4-[2'-(1-(4-cyano 3-trifluoromethylphenyl)-1H-tetrazol-5-yl)biphenyl-4-yl)methoxy]quinoline (in Example 15) and 2-ethyl-4-[(2'-(1-(4-pyridyl)-1H-tetrazol-5-yl)biphenyl-4-yl)methoxy]quinoline (in Example 16) respectively, there was obtained 2-ethyl-4-[(2'-(1H-tetrazol-5-yl)biphenyl-4-yl)methoxy]quinoline hydrochloride as a solid, in 38-40% yield.

EXAMPLES 17 and 18

These examples illustrate the production of a compound of the formula XV from a compound of formula IV.

EXAMPLE 17

Triethylamine (13.8 ml) was added to a mixture of 4-[(2-ethylquinolin-4-yloxy)methyl]phenylboronic acid hydrochloride (12.74 g), 2-bromobenzonitrile (5.92 g) and palladium chloride (0.13 g) in butanol (80 ml) and water (40 ml) and the mixture was heated at reflux for 3 hours. The hot reaction mixture was filtered through diatomaceous earth and the filtrate was stirred while allowing to cool to ambient temperature. The mixture was then cooled to 4° C. for 30 minutes. The solid which crystallised was collected by filtration, washed with cold butanol (16 ml) and water (2×16 ml) and then dried at 55° C. to give 4'-[(2-ethylquinolin-4-yloxy)methyl]biphenyl-2-carbonitrile (10.8 g); m.p. 161°-162° C.; NMR (CDCl3): 1.4(t,3H), 2.97(q,2H), 5.35(s,2H), 6.76(s,1H), 7.4-7.6(m,3H), 7.6-7.8(m,6H), 8.0(d,1H), 8.25(d,1H).

EXAMPLE 18

Tetrakis(triphenylphosphine)palladium (40 mg) was added to a suspension of 4-[(2-ethyl-5,6,7,8-tetrahydroquinolin-4-yl)oxymethyl]-phenylboronic acid (200 mg) and 2-bromobenzonitrile (106 mg) in toluene (2 ml) ethanol (0.5 ml) and 2M aqueous sodium carbonate (0.58 ml). The mixture was degassed and placed under an atmosphere of argon, then heated under reflux for 12 hours. The resulting solution was cooled to ambient temperature, and dichloromethane (30 ml) and water (10 ml) were added. The organic layer was separated, dried (MgSO4) and the solvent removed by evaporation. The residue was purified by flash chromatography, eluting with ethyl acetate/hexane (3:1 v/v), and the product triturated with ether/hexane to give 4-[(2'-cyanobiphenyl-4-yl)methoxy]-2-ethyl-5,6,7,8-tetrahydroquinoline (106 mg) as a white solid, m.p. 147°-148° C.; NMR (CDCl3): 1.29(t,3H), 1.7-1.95(m,4H), 5.17(s,2H), 6.57(s,1H), 7.4-7.7 (complex m,7H), 7.78(d,1H); mass spectrum (+ve CI) 369 (M+H)+.

EXAMPLES 19 and 20

These examples illustrate the production of a compound of the formula XI from a compound of the formula XVI.

EXAMPLE 19

A solution of 2-ethyl-4-[(2'-(2-tributylstannyl-2H-tetrazol-5-yl)biphenyl-4-yl)methoxy]quinoline in toluene (15 ml), prepared in situ by refluxing for 90 hours a mixture of 4'-[(2-ethylquinolin-4-yloxy)methyl]biphenyl-2-carbonitrile (0.9 g) and a solution of tributyltin azide in toluene (15 ml) [the latter prepared by reaction of tributyltin chloride (3.3 g) and sodium azide (1.13 g) in water (22.5 ml) at ambient temperature for 4 hours, followed by extraction with toluene and azeotropic removal of water from the extract to leave a volume of 15 ml], was added slowly over 1 hour to a solution of sodium nitrite (2.5 g) in water (10 ml) containing 12% w/v hydrochloric acid (10 ml), maintaining the temperature of the mixture below 5° C. A solution of sulphamic acid (1.43 g) in water (10 ml) was then added, maintaining the temperature below 5° C., and the mixture stirred for 1 hour. The resultant suspended semi-solid was collected by filtration and washed with water (3×10 ml), followed by toluene (10 ml). The semi-solid was then added to tetrahydrofuran (THF) (40 ml), which caused the product to dissolve and then crystallise as a white solid. After cooling for one hour the solid was collected by filtration, washed with THF (5 ml) and dried to give 2-ethyl-4-[(2'-(1H-tetrazol-5-yl)biphenyl-4-yl)methoxy]-quinoline hydrochloride; NMR similar to the product obtained from Example 10.

EXAMPLE 20

Hydrogen chloride was bubbled for 15 minutes through a solution of 2-ethyl-5,6,7,8-tetrahydro-4-[(2'-(2-tributylstannyl-2H-tetrazol-5-yl)biphenyl-4-yl)methoxy]quinoline in xylene [prepared by refluxing a mixture of 4-[(2'-cyanobiphenyl-4-yl)methoxy]-2-ethyl-5,6,7,8-tetrahydroquinoline (1.1 g) and tributyl tin azide (3.0 g) in xylene (3 ml) for 60 hours under an atmosphere of argon]. Volatile material was then removed by evaporation and the residue was recrystallised from methanol/ethyl acetate to give 2-ethyl-5,6,7,8-tetrahydro-4-[(2'-(1H-tetrazol-5-yl)bipheny-4-yl)methoxy]-quinoline hydrochloride (0.77 g); NMR (d6-DMSO): 1.3(t,3H), 1.7-1.9(m,4H), 2.6-2.7(m,2H), 2.9-3.0(m,4H), 5.5(s, 2H), 7.2(d,2H), 7.4(s,1H), 7.45(d,2H), 7.55-7.8 (complex m,4H).

Chemical Formulae

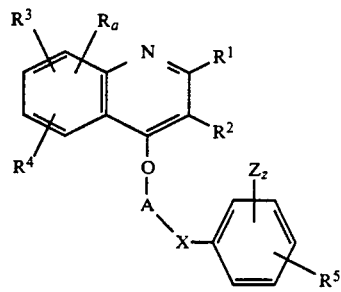

I

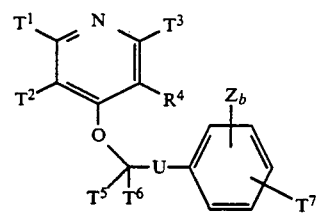

II

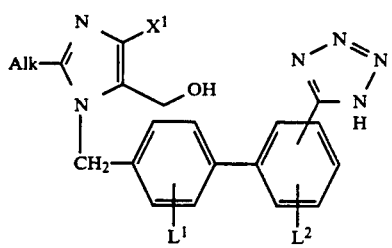

III

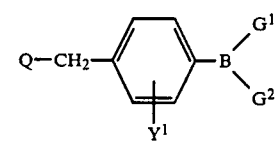

IV

-continued
Chemical Formulae

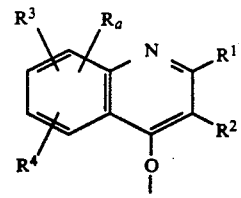

Va

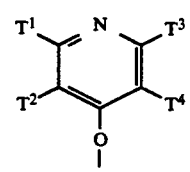

Vb

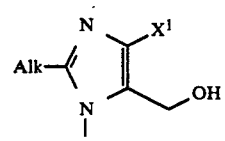

Vc

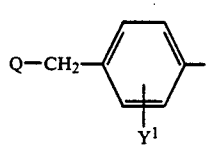

VI

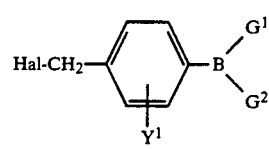

VII

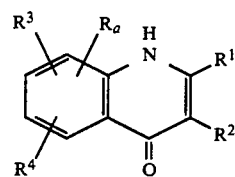

VIIIa

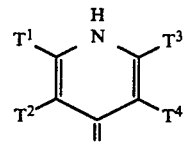

VIIIb

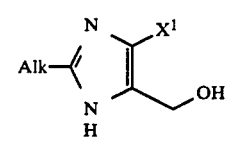

VIIIc

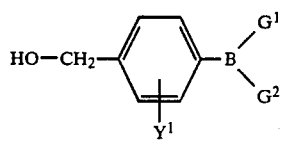

IX

-continued
Chemical Formulae

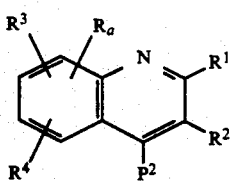

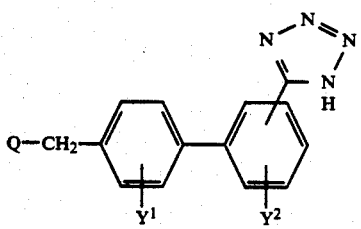

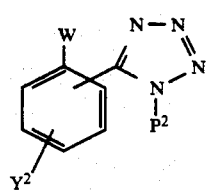

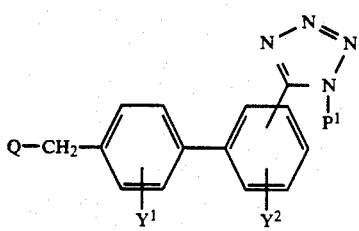

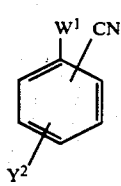

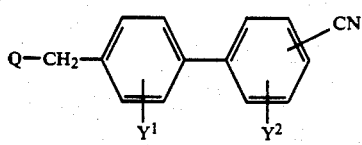

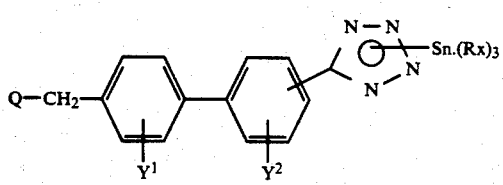

Scheme 1

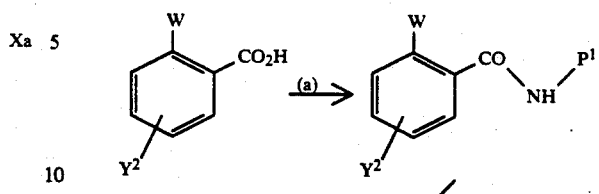

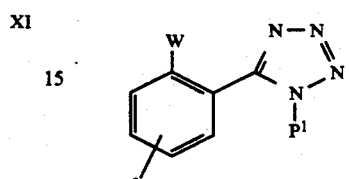

What we claim is:

1. A boron compound of formula IV

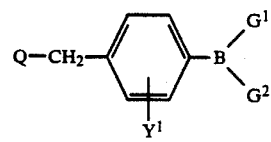

wherein Q is selected from:
(1) a 4-quinolyloxy moiety of the formula Va

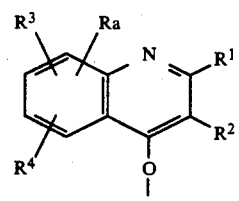

in which $R^1$ is hydrogen, (1-8C)alkyl, (3-8C)cycloalkyl, phenyl or substituted (1-4C)alkyl, the latter containing one or more fluoro substituents or bearing a (3-8C)cycloalkyl, hydroxy, (1-4C)alkoxy or phenyl substituent; $R^2$ is hydrogen, (1-8C)alkyl, (3-8C)cycloalkyl, (3-8C)cycloalkyl-(1-4C)alkyl, carboxy, (1-4C)alkoxycarbonyl, cyano, nitro, phenyl or phenyl(1-4C)alkyl; $R^3$ and $R^4$ are independently selected from hydrogen, (1-4C)alkyl, (1-4C)alkoxy, fluoro(1-4C)alkoxy, halogeno, hydroxy, trifluoromethyl, cyano, nitro, amino, (1-4C)alkanoylamino, alkylamino and dialkylamino of up to 6 carbon atoms, dialkylamino-alkyl of 3 to 8 carbon atoms, (1-4C)alkanoyl, carbamoyl, N-alkylcarbamoyl and di-(N-alkyl)carbamoyl of up to 7 carbon atoms, carboxy, (1-4C)alkoxycarbonyl, (1-6C)alkylthio, (1-6C)alkylsulphinyl, (1-6C)alkylsulphonyl, and substituted (1-4C)alkyl, the latter bearing an amino, hydroxy or (1-4C)alkoxy substituent; or $R^3$ and $R^4$ together form (1-4C)alkylenedioxy attached to adjacent carbon atoms of the benzene moiety of formula I; and Ra is selected from hydrogen, (1-4C)alkyl, (1-4C)alkoxy, halogeno, trifluoromethyl, cyano or nitro; and
(2) a 4-pyridyloxy moiety of the formula Vb

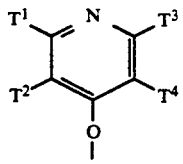

in which
T¹ is hydrogen, (1-8C)alkyl, (3-8C)cycloalkyl, phenyl or substituted (1-4C)alkyl, the latter containing one or more fluoro substituents or bearing a (3-8C)cycloalkyl, (1-4C)alkoxy or phenyl substituent; T² is hydrogen, (1-8C)alkyl, (3-8C)cycloalkyl, (3-8C)cycloalkyl-(1-4C)alkyl, carboxy, (1-4C)alkoxycarbonyl, (3-6C)alkenyloxycarbonyl, cyano, nitro, phenyl or phenyl(1-4C)alkyl; T³ is selected from halogeno, (1-4C)alkoxy, amino, alkylamino and dialkylamino of up to 6 carbon atoms, and any of the values defined for T¹; T⁴ is selected from hydrogen, (1-4C)alkyl optionally bearing an amino, (1-4C)alkanoylamino, phenylcarbonylamino, hydroxy or (1-4C)alkoxy substituent, carboxy, (1-4C)alkoxycarbonyl, (3-6C)alkenyloxycarbonyl, cyano, nitro, carbamoyl, (1-4C)alkanoyl, N-alkylcarbamoyl and di-(N-alkyl)carbamoyl of up to 7 carbon atoms, formyl, halogeno, amino, alkylamino and dialkylamino of up to 6 carbon atoms, 3-(1-4C)alkylureido and (1-4C)alkanoylamino; or T⁴ is a group of the formula -A¹.A².E wherein A¹ is carbonyloxy, A² is (1-6C)alkylene and E is selected from hydroxy, (1-4C)alkoxy, phenyloxy, phenyl(1-4C)alkoxy, pyridyl(1-4C)alkoxy, 4-morpholino(1-4C)alkoxy, phenylamino, amino, alkylamino and dialkylamino of up to 6 carbon atoms, (1-4C)alkanoylamino, (1-4C)alkylsulphonylamino, phenylsulphonylamino, sulphamoylamino (—NH.SO₂.NH₂), carboxamidomethylamino (—NH.CH₂.CO.NH₂), (1-4C)alkanoyloxy, phenylcarbonyloxy, aminocarbonyloxy (—O.CO.NH₂), (1-4C)alkylaminocarbonyloxy, carboxy, (1-4C)alkoxycarbonyl, carbamoyl, N-alkylcarbamoyl and di-(N-alkyl)carbamoyl of up to 7 carbon atoms, (1-4C)alkanoyl, 4-morpholino, 1-imidazolyl and succinimido group; or E is a group of the formula -A³.E¹ wherein A³ is oxy, oxycarbonyl or imino and E¹ is a 5 or 6-membered saturated or unsaturated heterocyclic ring containing 1 or 2 nitrogen atoms and linked to A³ by a ring carbon atom; or A³ is oxycarbonyl and E¹ is a 4-morpholino group or a 5 or 6-membered saturated heterocyclic ring containing 1 or 2 nitrogen atoms, optionally bearing a (1-4C)alkyl group and linked to A³ by a ring nitrogen atom; and wherein E¹ the remainder of the ring atoms are carbon; or T³ and T⁴ together form (3-6C)alkylene, one of the methylene groups of which may optionally be replaced by a carbonyl group, or (3-6C)alkenylene;
Y¹ is selected from hydrogen, (1-4C)alkyl, (1-4C)alkoxy, halogeno, (1-4C)alkanoyl, trifluoromethyl, cyano and nitro; and
G¹ and G² are independently selected from a hydroxy, (1-4C)alkoxy, (1-6C)alkyl and phenyl group, the latter optionally substituted by an (1-4C)alkyl, (1-4C)alkoxy or halogeno group; or G¹ together with G² forms an (1-4C)alkylenedioxy group attached to the boron atom, a methylene group of which may optionally bear 1 or 2 (1-4C)alkyl groups; or G¹ and G² together with the boron atom to which they are attached complete a 4- or 6-membered ring of alternate boron and oxygen atoms wherein each boron atom of the ring bears an identical group of the formula VI

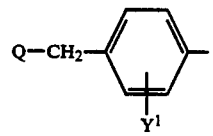

wherein Q and Y¹ have any of the meanings defined above; or an acid or base addition salt thereof.

2. A compound as claimed in claim 1 wherein Q is selected from:
(1) a 4-quinolyloxy moiety of the formula Va in which R¹ is (1-4C)alkyl and R², R³, R⁴ and Ra are all hydrogen; and
(2) a 4-pyridyloxy moiety of the formula Vb in which T¹ is (1-8C)alkyl; T² is hydrogen, unsubstituted phenyl or phenyl bearing one or two substituents independently selected from methyl, ethyl, methoxy, ethoxy, fluoro, chloro, bromo, iodo, cyano and trifluoromethyl; T³ is (1-8C)alkyl; T⁴ is hydrogen, (1-4C)alkoxycarbonyl or (3-6C)alkenyloxycarbonyl; or T³ and T⁴ together form trimethylene or tetramethylene.

3. A compound as claimed in claim 1 wherein Q is selected from:
2-methyl-4-quinolyloxy, 2-ethyl-4-quinolyloxy, 2-ethyl-6-methoxy-4-quinolyloxy, 6,7-dimethoxy-2-ethyl-4-quinolyloxy, 2-ethyl-5,6,7-trimethoxy-4-quinolyloxy, 2-ethyl-6-hydroxy-4-quinolyloxy, 2-ethyl-6-methylthio-4-quinolyloxy, 2-ethyl-7-hydroxymethyl-4-quinolyloxy, 2-ethyl-6-(2-fluoroethoxy)-4-quinolyloxy, 2-ethyl-6-carboxamido-4-quinolyloxy, 2-ethyl-6-fluoro-4-quinolyloxy, 2-ethyl-6-isopropoxy-4-quinolyloxy, 6-aminomethyl-2-ethyl-4-quinolyloxy, 2,6-dimethyl-3-methoxycarbonyl-4-pyridyloxy, 2-ethyl-5,6,7,8-tetrahydro-4-quinolyloxy, 6,7-dihydro-2-methyl-5H-cyclopentapyrid-4-yloxy, 2-ethyl-6-methyl-3-methoxycarbonyl-4-pyridyloxy, 6-ethyl-2-methyl-3-methoxycarbonyl-4-pyridyloxy, 2,6-dimethyl-3-methoxycarbonyl-4-pyridyloxy, 6,7-dihydro-2-ethyl-5H-cyclopentapyrid-4-yloxy, 2,6-dimethyl-3-phenyl-4-pyridyloxy, and 2,6-dimethyl-3-allyloxycarbonyl-4-pyridyloxy.

4. A compound as claimed in claim 1, 2 or 3 in which G¹ and G² are independently selected from hydroxy, methoxy, ethoxy, methyl, ethyl, propyl, isopropyl, butyl, tert-butyl and phenyl, the latter optionally substituted by an methyl, ethyl, methoxy, ethoxy, fluoro, chloro or bromo group; or G¹ together with G² forms a group of the formula —O—CH₂—O—, —O—CH₂—CH₂—O—, —O—CH₂—CH₂—CH₂—O— or —O—CH₂—C(CH₃)₂—CH₂—O— attached to the boron atom; or G¹ and G² together with the boron atom to which they are attached complete a 4- or 6-membered ring of alternate boron and oxygen atoms wherein each boron atom of the ring bears an identical group of the formula VI wherein Q and $Y^1$ have any of the meanings defined above; and $Y^1$ is selected from hydrogen, methyl, ethyl, methoxy, ethoxy, fluoro, chloro, bromo, formyl, acetyl, propionyl, trifluoromethyl, cyano and nitro.

5. A compound as claimed in claim 1 wherein $G^1$ and $G^2$ are both hydroxy or $G^1$ and $G^2$ together form an (1-4C)alkylenedioxy group.

6. A compound as claimed in claim 1 wherein Q is 2-ethyl-4-quinolyloxy or 2-ethyl-5,6,7,8-tetrahydro-4-quinolyloxy.

7. A compound of the formula IV selected from:
4-[(2-ethylquinolin-4-yloxy)methyl]phenylboronic acid;
2-(4-[(2-ethylquinolin-4-yloxy)methyl]phenyl)-5,5-dimethyl-1,3,2-dioxaborinane; and
4-[(2-ethyl-5,6,7,8-tetrahydroquinolin-4-yl)oxymethyl]phenylboronic acid; or an acid or base addition salt thereof.

* * * * *

UNITED STATES PATENT AND TRADEMARK OFFICE
CERTIFICATE OF CORRECTION

PATENT NO. : 5,245,035

DATED : September 14, 1993

INVENTOR(S) : Hiroyoshi HIDAKA, et al.

It is certified that error appears in the above-identified patent and that said Letters Patent is hereby corrected as shown below:

Title page, left column, Item 73, after "Japan" insert

-- and Tobishi Yakuhin Kogyo Kabushiki Kaisha, Tokyo, Japan --.

Signed and Sealed this

Second Day of August, 1994

Attest:

BRUCE LEHMAN

*Attesting Officer*     *Commissioner of Patents and Trademarks*